US007922899B2

(12) United States Patent
Vasta et al.

(10) Patent No.: US 7,922,899 B2
(45) Date of Patent: Apr. 12, 2011

(54) MEDICAL APPARATUS AND METHOD FOR SETTING UP A MEDICAL APPARATUS

(75) Inventors: Alessandro Vasta, Modena (IT); Roberto Gazzotti, Cavezzo (IT); Giovanni Paolo Cavicchioli, Medolla (IT)

(73) Assignee: Gambro Lundia AB, Lund (SE)

( * ) Notice: Subject to any disclaimer, the term of this patent is extended or adjusted under 35 U.S.C. 154(b) by 692 days.

(21) Appl. No.: 11/916,655

(22) PCT Filed: Jun. 9, 2005

(86) PCT No.: PCT/IB2005/001617
§ 371 (c)(1),
(2), (4) Date: Dec. 5, 2007

(87) PCT Pub. No.: WO2006/131775
PCT Pub. Date: Dec. 14, 2006

(65) Prior Publication Data
US 2008/0209357 A1      Aug. 28, 2008

(51) Int. Cl.
*B01D 17/12*     (2006.01)
*G06F 3/041*     (2006.01)
*G06T 1/60*      (2006.01)

(52) U.S. Cl. ...... 210/143; 210/85; 210/96.2; 210/321.6; 210/646; 604/4.01; 345/173; 345/530; 345/531; 700/2; 700/3; 707/687; 709/208; 715/700; 715/716

(58) Field of Classification Search .............. 210/85–87, 210/94, 96.2, 143, 321.6, 321.65, 645, 646, 210/929; 604/4.01, 5.01, 6.09, 65, 67; 345/168, 345/169, 172, 173, 530, 531; 700/2, 3, 79, 700/83, 213; 715/771, 700, 716, 719; 709/208, 709/211; 707/687, 770, 771
See application file for complete search history.

(56) References Cited

U.S. PATENT DOCUMENTS

| 4,228,506 A | | 10/1980 | Ripley et al. |
| 4,291,388 A | | 9/1981 | Ecker, Jr. et al. |
| 4,464,172 A | * | 8/1984 | Lichtenstein ............. 604/65 |
| 4,990,258 A | * | 2/1991 | Bjare et al. ............. 210/647 |
| 5,247,434 A | | 9/1993 | Peterson et al. |
| 5,276,611 A | | 1/1994 | Ghiraldi |
| 5,300,093 A | * | 4/1994 | Koestner et al. ........... 607/32 |
| 5,326,476 A | * | 7/1994 | Grogan et al. ............ 210/646 |
| 5,486,286 A | | 1/1996 | Peterson et al. |
| 5,487,827 A | | 1/1996 | Peterson et al. |
| 5,546,582 A | | 8/1996 | Brockmeyer et al. |
| 5,564,012 A | | 10/1996 | Shigyo et al. |
| 5,581,687 A | | 12/1996 | Lyle et al. |

(Continued)

FOREIGN PATENT DOCUMENTS
DE     197 42 633 A1     4/1999
(Continued)

*Primary Examiner* — Joseph W Drodge
(74) *Attorney, Agent, or Firm* — Pearne & Gordon LLP

(57) ABSTRACT

A medical apparatus comprises a user interface for setting parameters and includes: a screen for visualizing values of said parameters, a main control unit connected to the interface, a first memory and a video memory both connected to the main control unit for storing data corresponding to images on screen; the main control unit allows setting of a new value for a parameter, displays the new value on a screen region, stores the new value in the first memory, captures from the video memory data representative of said screen region, verifies from said representative data if the displayed value corresponds to the value in the first memory. A method for setting up a medical apparatus is also disclosed.

56 Claims, 4 Drawing Sheets

U.S. PATENT DOCUMENTS

| | | | |
|---|---|---|---|
| 5,617,534 | A | 4/1997 | Balmer et al. |
| 5,788,851 | A | 8/1998 | Kenley et al. |
| 5,858,239 | A | 1/1999 | Kenley et al. |
| 5,903,211 | A | 5/1999 | Flego et al. |
| 5,956,023 | A | 9/1999 | Lyle et al. |
| 6,143,181 | A | 11/2000 | Falkvall et al. |
| 6,144,837 | A | 11/2000 | Quy |
| 6,146,523 | A | 11/2000 | Kenley et al. |
| 6,230,058 | B1 | 5/2001 | Legay |
| 6,256,643 | B1 | 7/2001 | Cork et al. |
| 6,284,131 | B1 | 9/2001 | Hogard et al. |
| 6,363,290 | B1 | 3/2002 | Lyle et al. |
| 6,381,557 | B1 | 4/2002 | Babula et al. |
| 6,468,241 | B1 | 10/2002 | Gelfand et al. |
| 6,542,910 | B2 | 4/2003 | Cork et al. |
| 6,610,024 | B1 | 8/2003 | Benatti |
| 6,685,664 | B2 | 2/2004 | Levin et al. |
| 6,695,806 | B2 | 2/2004 | Gelfand et al. |
| 6,738,052 | B1 | 5/2004 | Manke et al. |
| 6,773,412 | B2 | 8/2004 | O'Mahony et al. |
| 6,775,577 | B2 | 8/2004 | Crnkovich et al. |
| 6,811,707 | B2 | 11/2004 | Rovatti et al. |
| 7,033,539 | B2 * | 4/2006 | Krensky et al. .................. 422/44 |
| 7,549,961 | B1 * | 6/2009 | Hwang ........................ 600/440 |
| 2002/0052548 | A1 | 5/2002 | Hsu et al. |
| 2002/0147423 | A1 | 10/2002 | Burbank et al. |
| 2002/0151804 | A1 | 10/2002 | O'Mahony et al. |
| 2003/0093744 | A1 | 5/2003 | Leung et al. |
| 2003/0152482 | A1 | 8/2003 | O'Mahony et al. |
| 2003/0218623 | A1 | 11/2003 | Krensky et al. |
| 2004/0084358 | A1 | 5/2004 | O'Mahony et al. |
| 2004/0095507 | A1 * | 5/2004 | Bishop et al. .................. 348/441 |
| 2005/0237330 | A1 * | 10/2005 | Stauffer et al. ................ 345/531 |
| 2005/0251424 | A1 * | 11/2005 | Sanders et al. .................... 705/3 |

FOREIGN PATENT DOCUMENTS

| | | |
|---|---|---|
| DE | 100 13 666 A1 | 10/2001 |
| EP | 0 384 155 A2 | 8/1990 |
| EP | 0 556 805 A2 | 8/1993 |
| FR | 2 645 296 A1 | 10/1990 |
| JP | 1 079 833 A | 3/1989 |
| JP | 2 278 466 A | 11/1990 |
| JP | 3 109 648 A | 5/1991 |
| JP | 7 084 829 A | 3/1995 |
| JP | 9 047 447 A | 2/1997 |
| WO | WO 96/41292 A1 | 12/1996 |
| WO | WO 99/49919 A1 | 10/1999 |

* cited by examiner

MEDICAL APPARATUS AND METHOD FOR SETTING UP A MEDICAL APPARATUS

TECHNICAL FIELD

The invention relates to a medical apparatus and to a method for setting up a medical apparatus. The medical apparatus of the invention could be an apparatus intended for the extracorporeal treatment of blood, for instance by hemodialysis, hemofiltration, hemodialfitration, ultrafiltration, plasmapheresis or an apparatus for processing whole blood and/or blood components.

BACKGROUND ART

Blood treatment apparatus and similar medical devices comprise an extracorporeal circuit, provided with at least one blood treatment or blood processing unit, one tube, connecting a blood removal zone to said unit, and a second tube, extending downstream of the treatment or processing unit towards a blood return zone to the patient or towards a blood/blood components collection zone. Blood is moved from the patient or donor to the treatment or processing unit via pumps or other actuators controlled by the machine.

In case the machine is for instance a hemodialysis apparatus, then for achieving the required treatment of blood, an adequately prepared dialysis liquid shall be sent to the treatment unit, water removal through the treatment unit membrane as well other machine parameters shall be controlled. Depending upon the type of hemodialysis machine and upon the type of treatment, a user can have the possibility to set a number of parameters in order to impose a specific prescription to a patient, such as for instance: flow rates of the various liquids, temperatures and conductivity of the liquids, concentration of the liquids used during treatment, flow rates of any anticoagulants used and delivered during treatment, pressures in the fluid conduits, net liquid removal rates of plasma water from whole blood and so on.

It is therefore evident that users (the patient himself, a physician, a nurse) have normally a plurality of parameters to set before or even during the process performed by the medical apparatus. Moreover it is clear that easy and safe, data entry as well as data storage and transmission are particularly important in machines as blood treatment machines or blood processing apparatus where the process executed by the machine acts on a patient or donor blood. Particularly in case of treatment of blood of patients suffering from kidney failure the patient is constantly connected to the machine with the serious risk that any failure in entering or in actuating a proper prescription could have negative impacts on the treatment delivery and on patient's health.

In this situation several technical solutions have been developed in the past in order to render easy and reliable data entry in blood treatment or blood processing apparatus. A first known method for entering data in a dialysis machine is described in U.S. Pat. No. 5,247,434. This method comprises the following steps:

(a) providing a touch screen interface with an indicium thereon corresponding to a treatment parameter;
(b) touching the indicium;
(c) in response to said touching, invoking a data entry pad on a region of the touch screen;
(d) entering a parametric value corresponding to the treatment parameter by touching one or more buttons of the data entry pad;
(e) touching a first region of the data entry pad to signal entry of the parametric value;
(f) displaying on the touch screen a button soliciting verification of the newly entered parametric value;
(g) touching the button soliciting verification; and
(h) in response to steps (b)-(g), causing the parametric value corresponding to the treatment parameter to be changed.

In other words before really implementing the change the user is solicited to verify the newly entered parameter and press a button confirming the change.

The same patent also discloses a method for entering variable parameters, i.e. parameters that can vary in the course of time during treatment.

More in detail U.S. Pat. No. 5,247,434 shows a method of programming a time-varying parameter comprising the steps:

(a) providing a touch screen interface;
(b) displaying on the touch screen first and second axes, the first axis corresponding to the time-varying parameter, the second axis corresponding to time;
(c) touching the touch screen at a plurality of points to define points on a parameter-versus-time curve;
(d) presenting on the touch screen a series of bars corresponding to said curve;
(e) selecting one of said bars for alteration;
(f) displaying on the screen a numeric parameter corresponding to the selected bar;
(g) touching the screen at first or second locations to increase or decrease, respectively, the displayed numeric parameter and thereby alter the value of the numeric parameter to which the selected bar corresponds;
(h) touching the screen at a third location to signify completion of steps (b)-(g); and
(i) storing data corresponding to the bars in a memory to which the process-control system can refer in changing the time-varying parameter with time.

From document U.S. Pat. No. 5,326,476 is known a further method for entering a time variable parameter, ultrafiltration in particular, in a hemodialysis machine, having a programmable memory and having ultrafiltration capability, so as to enable the machine to perform ultrafiltration of fluid from a patient according to a time-variable ultrafiltration profile. The method disclosed in U.S. Pat. No. 5,326,476 comprises the following steps:

(a) entering into the programmable memory a prescribed time for dialysis;
(b) entering into the programmable memory a target ultrafiltration volume of fluid to be removed from the patient;
(c) entering into the programmable memory a proposed ultrafiltration profile being representable as a plot of coordinates on an ultrafiltration rate axis and a time axis and defining a profile ultrafiltration volume; and
(d) shifting the proposed ultrafiltration profile along the ultrafiltration rate axis to the degree necessary to make the profile ultrafiltration volume equal to the target ultrafiltration volume, so as to allow the hemodialysis machine to achieve, while ultrafiltrating the fluid according to the shifted ultrafiltration profile, the entered target ultrafiltration volume within the entered prescribed time.

This method allows the user to enter a profile curve and to move the ultrafiltration profile along the ordinates so as to achieve the desired integral value in the desired time frame.

A further system for a dialysis machine is known from document U.S. Pat. No. 5,788,851 and comprises:

a touch screen displaying messages and information and permitting to select a parametric value pertinent to operation of said machine or pertinent to a treatment by said machine, one hard key off of said touch screen, said touch screen prompting a user to press said hard key to signify that the selection of the parametric value has been completed;

a control system having a host and a safety processing unit, wherein pressing of said hard key causes transfer of information relating to the selected parametric value from the host processing unit to the safety processing unit which is then checking said selected parametric value to confirm that said parametric value meets validation or safety criteria for a patient connected to said machine.

The above system is therefore using two processing units in order to insure that unsafe parameters values are entered into the machine.

It is also known from U.S. Pat. No. 6,811,707 using a dialysis machine wherein after entry of a value for a parameter the value is stored in at least two different memory locations connected to corresponding separate main control units. At predetermined intervals of time, one of the units sends the dialysis treatment parameters values stored in its memory to the other unit. The values are then compared and an alarm signal generated if the values of the same parameters in the two memories of the two units do not coincide with each other.

SUMMARY OF THE INVENTION

While the above disclosed systems and methods served to give the user possibility to enter data in a relatively easy manner and/or served to reduce data entry errors or data memorization errors, the present invention aims to further improve ease and reliability in data entry procedures, particularly for blood treatment machines.

Furthermore the invention aims to offer a reliable and automated procedure for verifying proper memorization of entries.

In an embodiment the invention aims to render reliable the storing of data on at least two distinct memory areas reducing the need for verification by the user.

Further characteristics and advantages will better emerge from the following description in relation to some preferred but non-exclusive embodiments of an apparatus according to the invention.

SHORT DESCRIPTION OF THE DRAWINGS

The description will be made with reference to the figures of the accompanying drawings, provided by way of non-limiting example, in which.

DETAILED DESCRIPTION

Figure 1:
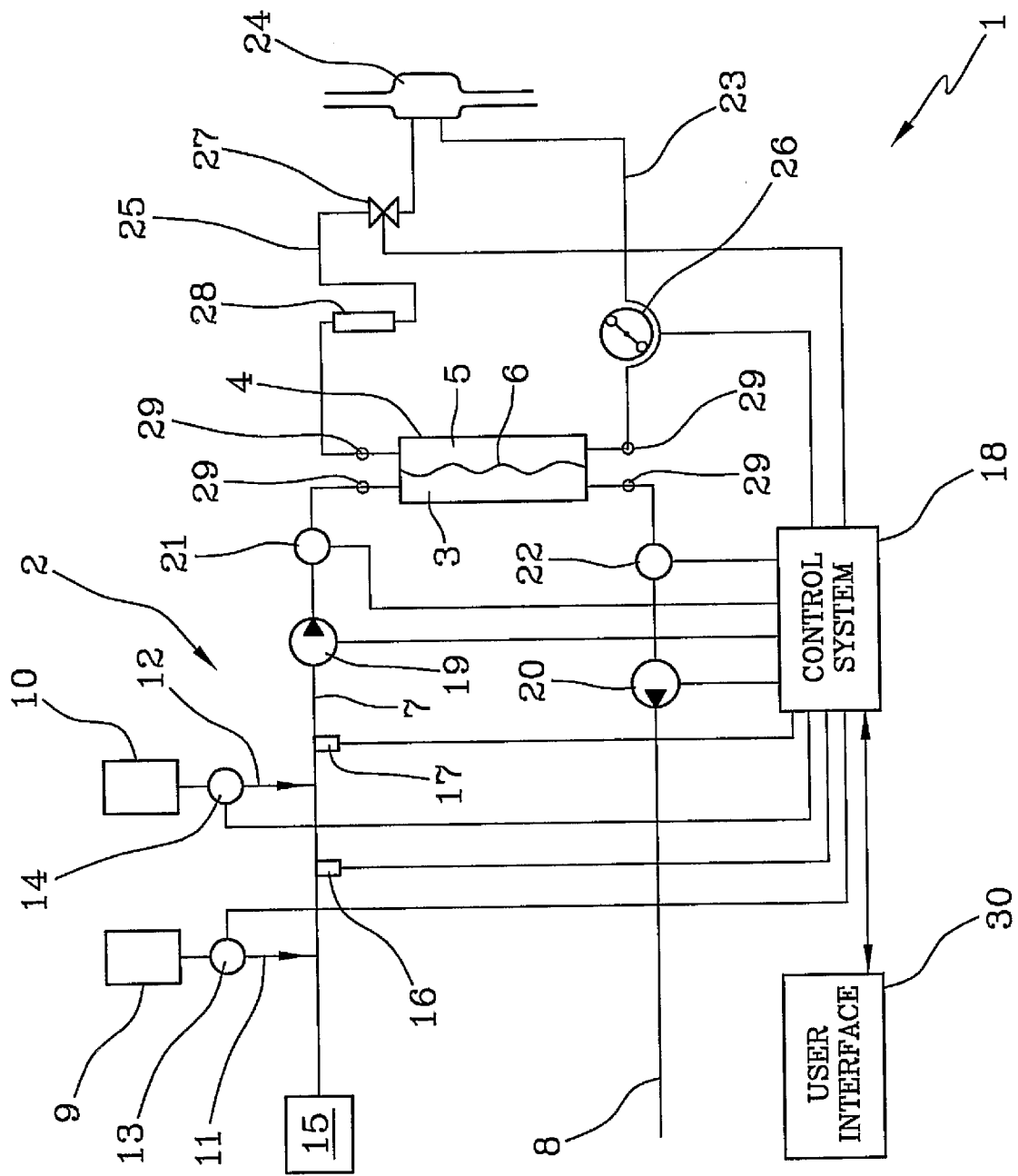
FIG. 1 is a schematic representation of a medical apparatus, for instance a blood treatment machine, according to the invention.

With reference to the figures, reference number 1 denotes a medical apparatus according to the invention.

The medical apparatus of the embodiment is a machine for the extracorporeal treatment of blood. Of course the medical apparatus of the invention could alternatively be a blood processing device or a blood component preparation device or a medical fluid delivery/collection device.

The apparatus shown in the enclosed drawings comprises a module 2 for preparing dialysis liquid to be sent into a first chamber 3 of a blood treatment unit 4, which is formed by a casing defining at least two chambers 3,5 separated by a semipermeable membrane 6. The dialysis preparation module 2 includes tubing 7 bringing dialysis liquid to the first chamber inlet, while a waste line 8 receives spent liquid exiting via an outlet of the first chamber. In detail, the module 2 includes one or more concentrate containers 9, 10 delivering concentrated solutions, via respective lines 11, 12 and upon the action of respective concentrate pumps 13, 14, into the tubing 7 thereby properly mixing water coming from a source 15 with said concentrates and obtaining the dialysis liquid. Conductivity or concentration sensors 16, 17 can be provided on tubing 7 downstream each respective concentrate line. Said sensors provide control signals to a control system 18 which is responsible to then act on the concentrate pumps. A pump 19 is generally operating on tubing 7 and a pump 20 on the waste line 8. Of course different alternative embodiments can be envisaged to bring dialysis liquid to the treatment unit with appropriate chemical and physical properties. For instance pre-prepared dialysis liquid bags could be used with no need of online preparation of dialysis liquid starting from concentrates and water. Fluid balance sensors, for instance a first and a second flow-meter 21, 22, operating on tubing 7 and on waste line 8 respectively, are used and are connected to the control system to provide signals necessary for regulating at least one of pumps 19, 20.

When the apparatus is in use, an extracorporeal blood circuit is connected to the second chamber 5. The extracorporeal circuit usually comprises at least one access branch 23 extending between a blood removal zone 24 from a patient or donor and the treatment unit 4, at least a return branch 25 extending downstream of the treatment unit, between the second chamber and a return zone of the blood to the patient; a peristaltic pump 26 is operatively associated to a length of pump tube of the extracorporeal circuit access branch. A clamp or other closure device can operate on the blood return branch 25, typically downstream of a gas separator 28.

Usually, at the removal and return branches of the blood to or from the patient, access means are provided to the cardiovascular system of the patient, for example constituted by needles of appropriate sizes, catheters or accesses of different types. One or more liquid infusion lines could be provided connected at one end to an infusion liquid source (a respective bag or an on-line infusion liquid preparation system) and at the other end to the extracorporeal circuit, or directly to the patient or donor. Other sensors, such as pressure sensors 29, can be provided either on the extracorporeal circuit and/or on the dialysis liquid side of the apparatus.

The apparatus 1 presents at least a user interface 30 for enabling setting of a plurality of parameters pertinent to operation of said apparatus or pertinent to a treatment to be performed by said apparatus.

Figure 2:
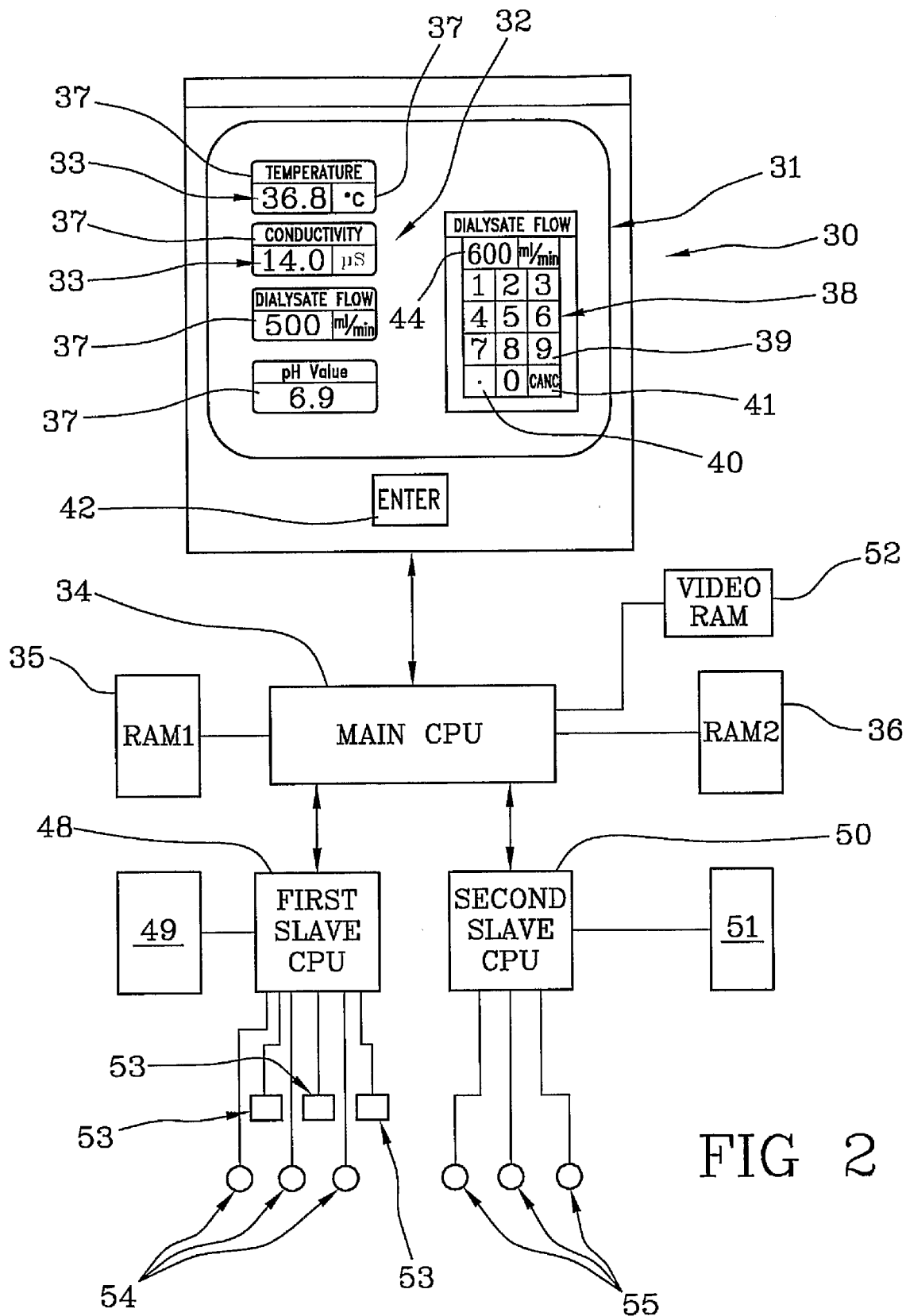
FIG. 2 is illustrating a user interface and, schematically, a control system of the apparatus of the present invention.

A non-limiting embodiment of a user interface is schematically represented in FIG. 2.

The user interface 30 includes a screen 31 for visualization of values of said parameters. In the exemplifying representation of the screen 31 of FIG. 2, four apparatus operation parameters 32 are displayed and can be set by the user, namely dialysis conductivity, temperature, pH and flow rate of the dialysis liquid. Of course the specific page shown on the screen of FIG. 2 is purely exemplifying and one among a plurality the apparatus is programmed to display in the course of apparatus set up for allowing data entry.

In detail the screen of the user interface is operable to show the set values 33 a user has input for the parameters available for modification. The screen can be a touch screen as in the embodiment shown in FIG. 2, or a normal CRT screen or a non-touch sensitive display device, depending upon the type of user interface, as it will be described here below in greater detail.

The activity of the user interface is determined by control system 18, which is connected to the user interface, is responsive to actions by a user on said user interface, and controls operations of the apparatus by acting on a plurality of actuators (such as pumps 12, 13, 19, 20, 27, valve 27 and others) and by receiving signals by a plurality of sensors (such as for instance sensors 12, 13, 21, 22, 29 etcetera).

The control system includes a main control unit 34, connected to the user interface 30, a first memory 35 connected to the main control unit, a second memory 36 connected to the main control unit, a video memory 52 also connected to the main control unit and specifically devoted for storing data corresponding to images visualized or to be visualized on the screen. From a technical point of view the main control unit includes a microprocessor, while the three above-mentioned memories can be in a single physical memory or in physically separated memory devices.

The main control unit executes in use a program that renders the unit able to carry out the following steps allowing a user to entry one or more settings for a number of parameters.

First, when executing said program, the control unit displays one or more indicia 37 on said screen corresponding to respective treatment parameters. The indicia can be icons representing the parameters or buttons or other specifically designated areas of the screen, which the user is allowed to select for identifying the parameter a user intends to modify. The selection of the indicium and therefore of the corresponding parameter can be done for instance by touching the indicium (if the screen is a touch screen or includes touch sensitive areas) or by acting on hard keys or hard toggles forming part of the user interface and operable for moving a cursor or for highlighting the indicium of the parameter a user intends to select. In the embodiment shown in FIG. 2, the touch screen 31 displays four button shaped indicia 37 which can be selected by touching the area of the screen delimited by each button. In FIG. 2 the dialysate flow button has been selected and the main control unit is programmed for sensing the selection (in this case the touch) made by the user and for moving the button from an unselected to a selected condition wherein said button is visually differentiated with respect to the unselected condition (this differentiation is not represented in FIG. 2 and may consist in one of the following: a modification of the background colour of the button compared to the unselected buttons background colour, and/or a modification of the border colour or thickness of the button compared to the unselected buttons border, and or a change in the shape of the selected button compared to the unselected ones, and/or a texturing of the selected button area, and/or a blinking of the selected button area or of parts thereof; of course any equivalent graphic means useful for emphasizing the selected condition can be adopted). Once an indicium and therefore a corresponding parameter has been selected for modification, the main control unit is also programmed for allowing setting of a new value for said parameter(s) and then storing the new value in the first memory 35. The new value can be entered in a number of ways, which will be here below described in detail.

According to a first solution, entry of a new setting for a parameter value comprises the following steps which are executed by the main control unit: the touch of the indicium is sensed and in response to said touching on the indicium the main control unit is programmed for invoking a data-entry pad 38 on the touch screen 31 (see FIG. 2). In order to allow modification of the value of the parameter or in order to allow first entry of a value, the data entry pad has a display region showing the value under modification and at least two set buttons 39, for instance keys allowing to increase or decrease the value in the display region. In the embodiment of FIG. 2 more then two buttons 39 are present on the data entry pad, each button representing a corresponding digit to ease the entry of a desired set value. One or more buttons 40 representing mathematical separators (comma or colon) and a cancel button 41 can also be present on the data entry pad. In any case, irrespective of the type of data entry pad, the control unit 34 is programmed for receiving a setting of a parametric value corresponding to the treatment parameter by touching one or more buttons of the data-entry pad. Once the setting has been completed the control unit detects the touching of an enter key 42 for signifying setting has been completed and entering the set value into the first memory 35. The enter key can be invoked on the data entry pad, or can be present in another part of the touch screen or, as shown in the embodiment of FIG. 2, said enter key can be an hardware enter button positioned off the area of the screen.

Figure 5:
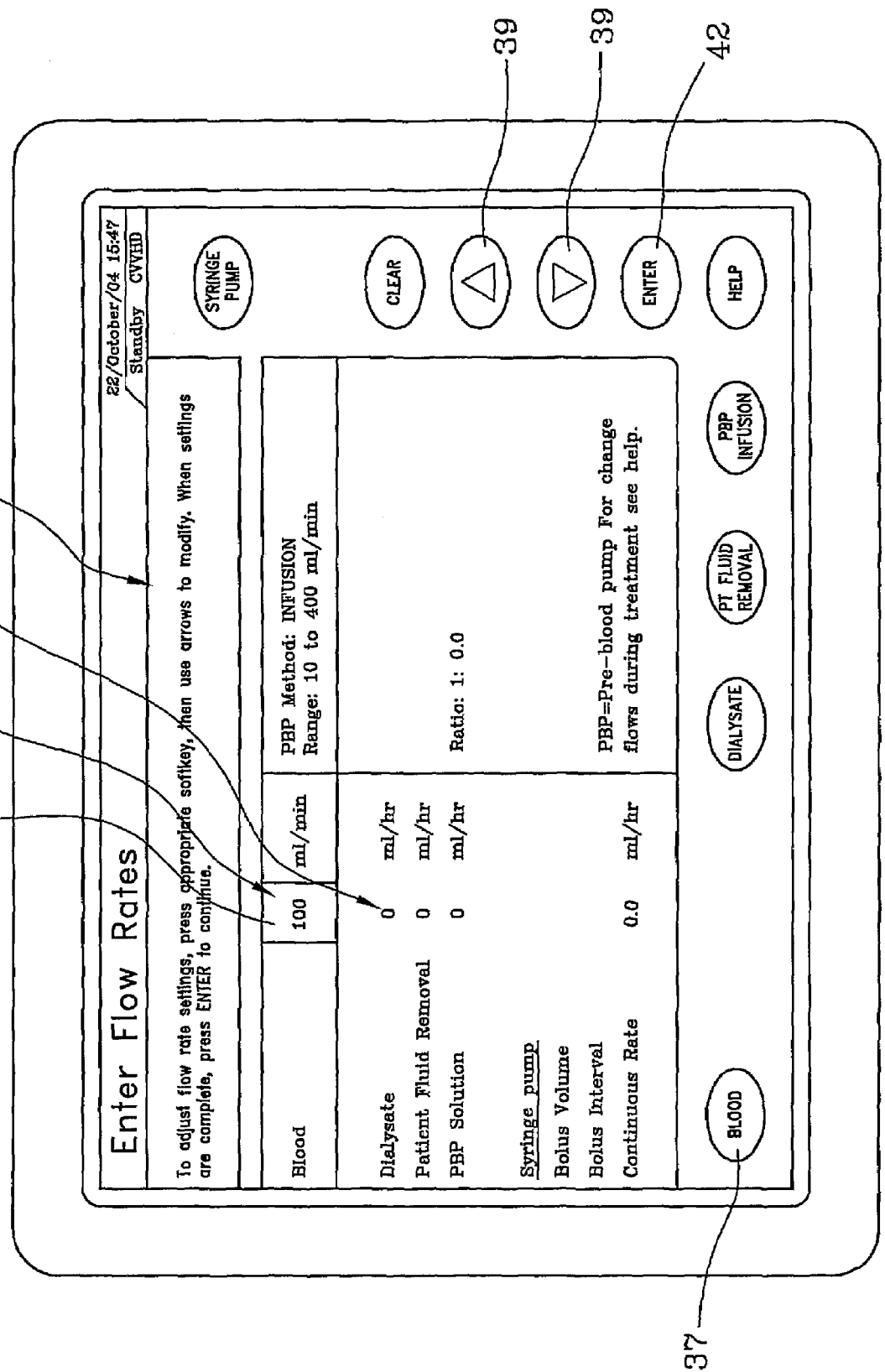
FIG. 5 shows an alternative embodiment of a user interface of an apparatus according to the invention.

According to a further alternative shown in FIG. 5 again adopting a touch screen 31, the main control unit 34 could be programmed for allowing entry of a parameter value according to the following steps. In response to a touching of a parameter indicium by the user the control unit is activating on the touch screen at least two set buttons 39 and an enter key 42 (these buttons and key could be already present on the touch screen and simply activated for modification of the selected parameter setting or could be invoked on the touch screen in response to said touching). No data entry pad is being invoked as the current value of the parameter(s) is shown on the screen in corresponding value display regions 43 even before selection of a specific parameter. In response to touching of a parameter indicium 37, in this case the one relating to the blood pump flow rate setting, a user can modify the setting by pressing one or both the arrow shaped buttons 39 on the right of the screen and then signify completion of the modification by pressing the enter key 42 on the touch screen. The main control unit detects the touching of said enter key for signifying setting has been completed and enters the newly set value in the first memory 35.

Once the value of the selected parameter has been modified and the new value entered, the main control unit is programmed for capturing from the video memory 37 data representative of a region 44 of the screen where the value of the entered parameter is being graphically displayed. Then the main control unit verifies if the value graphically displayed in the region 44 corresponds to the value stored in the first memory 35.

Figure 3:
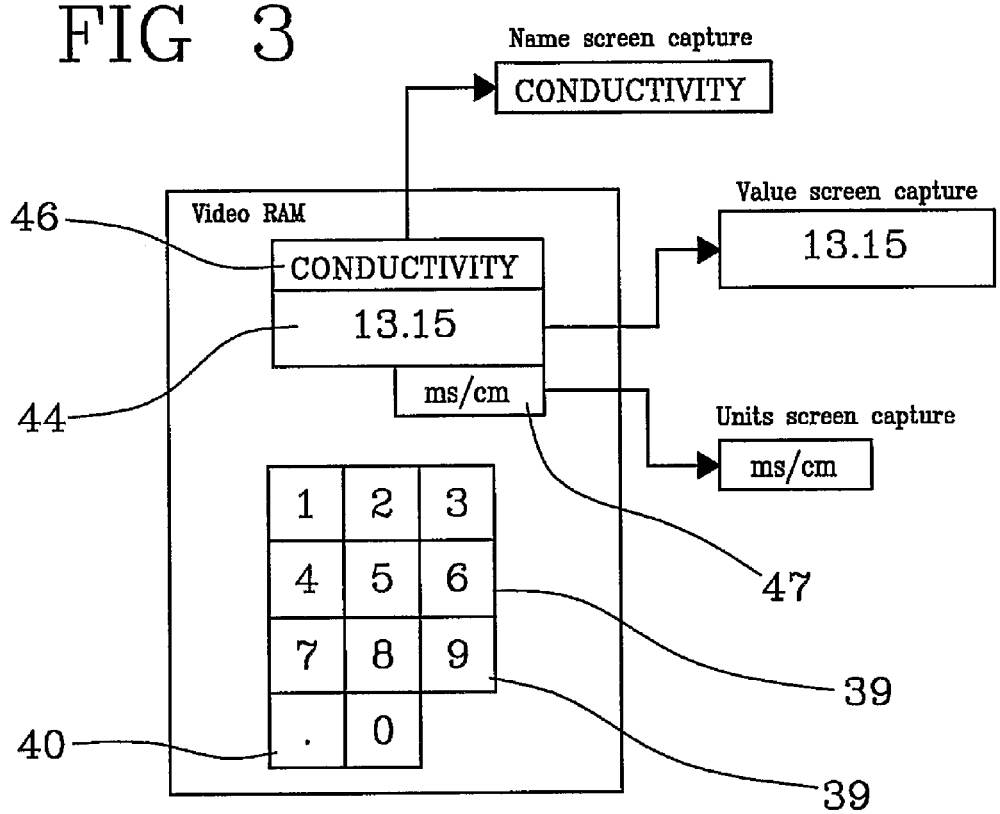
FIG. 3 is a block diagram showing a particular of the invention during a step of entering a new value for a parameter.

FIG. 3 emphasizes a particular of the touch screen and schematically shows the above step of capturing from the video memory the image displayed in region 44.

According to an auxiliary aspect of the invention the main control unit is programmed to execute a first and a second task, each comprising a number of operative steps.

The steps of allowing selection, modification and entry of the value in the first memory 35 are part of the first task executed in use by the main control unit.

The step of capturing data from the video memory and the verification step are part of the second task executed by the control unit.

In practice the first and the second task are two separate software routines executed in use by the main control unit. The two tasks are working with a high degree of independence from each other: indeed the second task is activated upon receipt from the first task of a new set message informing the second task that a new parameter value has been entered. According to an embodiment the control unit is programmed to work in multitasking mode: in particular the multitasking mode can be in time-share (in this case the control unit devotes prefixed time-shares to execute each task) or according to priority criteria. In any case it is advantageous that the message is sent by the first task only once the new value is stored in the first memory 35.

The second task activities (capture, verification and storing in the second memory) are activated only for a limited number of parameters. Indeed, the first task provides for a step of detecting if the value under modification refers to safety relevant parameters, which are a subset of said plurality of parameters, and sends the message triggering activation of the second task only in case of modification in the setting of safety relevant parameters.

Referring by way of non limiting example to the blood treatment apparatus of FIG. 1, the safety relevant parameters are one or more selected in the group comprising: temperature of the dialysis liquid, conductivity of the dialysis liquid, flow rate of the dialysis liquid, flow rate of the spent dialysate, flow rate of the blood in the extracorporeal circuit, ultrafiltration rate through the semipermeable membrane, net weight loss rate, treatment time, total weight loss.

Figure 4:
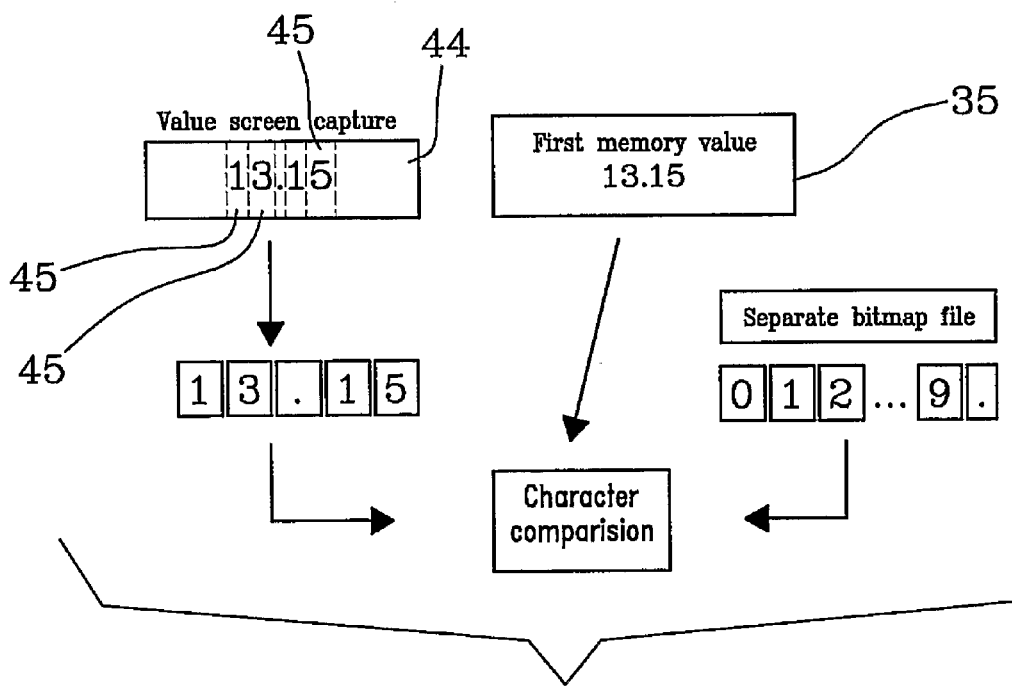
FIG. 4 shows, again in form of block diagram, a further step carried out by the apparatus of the invention following entry of a new value for a parameter.

Going now into a more detailed description, it should be noticed that after said verification step the second task also includes a step of storing the value in the second memory 36 if verification reveals identity between the value graphically represented in said region and the value entered in the first memory 35. Moreover if said verification reveals identity between the value graphically represented in said region and the value entered in the first memory, the main control unit is programmed to execute a step of displaying on a zone of the screen distinct from said region the value stored either in the first memory or in the second memory. The verification step includes the steps of recognizing from said data the numeric value graphically represented in said region and comparing said numeric value to the entered value of the parameter stored in the first memory. FIG. 4 shows that the region 44 of the screen where the value of the entered parameter is being displayed is separated in areas 45, each area being intended for the graphic representation of a single character forming said value. The main control unit recognizes the value displayed and contained in the video memory by referring to a plurality of sets of graphic data (for instance each set of graphic data can be a bitmap of each character expected to be entered by a user, including digits, mathematical symbols, mathematical operators). According to a preferred embodiment, the recognition includes two sub-steps, namely the control unit first compares the captured data with pre-stored data patters: in so doing it is possible to see if known patters have been captured; in case the captured data do not match with anyone of the pre-stored data pattern, then an alarm is generated. As a second step, if a known pattern is recognized, the corresponding character or set of characters is assigned.

Notice that the main control unit compares the captured data referring to each area with the sets of graphic data for identifying the character corresponding to each sub-area. Once the characters displayed in each sub-area 45 have been determined, then a character by character comparison with the value for the corresponding parameter stored in the first memory is possible; alternatively the control unit can assemble the identified characters to form the numeric value displayed in said area and compare it with the corresponding value in the first memory 35.

As an alternative to the above described procedure, the control unit could be programmed to consider the region 44 as a single area, compare the data representing the value displayed in said single area with known patterns and then if the value matches with one known pattern further proceed to checking if the value stored in the first memory corresponds to the value displayed in region 44.

According to a further alternative the verification step includes the steps of converting the value entered in the first memory in data graphically representing said value and comparing the data graphically representing the value entered in the first memory to said graphic data representative of the region of the screen where the value of the entered parameter is being displayed. In other words instead of converting the graphic data from the video memory 37 into a value and then compare two values, it is possible to apply the above mentioned bitmaps and graphically transform the value contained in the first memory into a graphic image as if it were to be displayed on a screen for then executing a comparison of the graphic image with the one in the video memory resulting from region 44 capture.

In addition (please refer again to FIG. 3 embodiment) to the capture of the region 44 of the screen where the value is being displayed, the main control unit can also be programmed for capturing from video memory second data representative of a second region 46 of the screen where the name of the entered parameter is being displayed, and verifying if the name graphically displayed in said second region corresponds to a pre-stored name for the same parameter; also in this case if the verification step is positively passed, then the main control unit stores the name in the second memory 36.

It is to be noted that in order to discriminate the parameter name the control unit makes reference to pre-stored patterns of known characters as for the detection of the value. As mentioned once the name displayed is recognized, the control unit compares said name with a pre-stored reference name for the same parameter to check whether there is identity or not. In case of name recognition, pre-stored names and pre-stored patterns of known data could significantly vary depending upon the language. It is therefore advantageous to store said reference pre-stored names and said reference pre-stored patterns on mass memory devices such as a flash memory, a hard disk, rewritable optical data carriers or other alternative mass storage means connected to the main control unit. In this way it is possible storing names and patterns customized to the language adopted by the machine, without changing the working of the control system. The mass storage device can be easily updated for new languages and or for enabling recognition of further names and patterns.

Furthermore the main control unit can be programmed for capturing from video memory third data representative of a third region 47 of the screen where the unit of measure (for instance a physical or chemical unit of measure) of the entered parameter is being displayed and for verifying if the unit graphically displayed in said third region corresponds to a pre-stored unit stored for the same parameter; if the verification step is positively passed, then the control unit stores the unit of measure in the second memory.

It is to be noted that in order to discriminate the unit of measure the control unit makes reference to pre-stored patterns of known characters as for the detection of the value or of the parameter name. Once the unit displayed is recognized, the control unit compares said unit with a pre-stored reference unit for the same parameter to check whether there is identity or not. In case of unit of measure recognition, pre-stored units and pre-stored patterns of known data could significantly vary depending upon the language and or the unit system adopted. It is therefore advantageous to store said reference pre-stored units of measure and said reference pre-stored patterns on mass memory devices such as a flash memory, a hard disk, rewritable optical data carriers or other alternative mass storage means connected to the main control unit. In this way it is possible storing units of measure and patterns customized to the language and unit system adopted by the machine, without changing the working of the control system. The mass storage device can be easily updated for new languages/unit systems and or for enabling recognition of further names and patterns.

As above described the starting of the screen region capturing step is triggered by a new set message sent by the first to the second task: in particular, the new set message contains the following information allowing the second task to perform the screen region capture:

information relating to the identity of message and of the parameter under modification,
information relating to coordinates $(x_1, y_1, x_2, y_2)$ of the screen region where the value is displayed.

In case also the second and third regions are to be captured, the message would contain also information on the coordinates $(x_1, y_1, x_2, y_2)$ of the screen region where the name is displayed and on coordinates $(x_1, y_1, x_2, y_2)$ of the screen region where the unit of measure is displayed.

While in the above exemplifying embodiment Cartesian coordinates are used, alternative coordinates such as polar systems or other equivalent coordinates serving to identify a region can be used.

In order to further increase safety of the apparatus the following further features are provided with.

The main control unit is indeed programmed for periodically comparing the values of the parameters in the first memory to the values of the corresponding parameters in the second memory. In detail in the embodiments herein described it is the second task responsible for activating the comparison between values of the safety relevant parameters in the second memory with the corresponding values of safety relevant parameters in the first memory. When discrepancies are detected a consecutive number of times, then the second task can activate an alarm procedure, which is not disclosed in detail as it does not form part of the present invention.

According to a further feature the main control unit is also programmed for running a step of range checking to verify if the value that is being set is within a predetermined range of acceptable values, and a subsequent step of activating the possibility to enter in the first memory said set value only if said range checking step is positively passed. In other words the user is prevented to enter in the first memory an out of range value as the first task operated by the main control unit checks if the value under modification is within a proper range. This is obtained by the main control unit either checking the entered value and activating the enter key only if the entered value is in a permissible range or by said unit preventing the user to even set an out of range value.

Even though the first task executed by the control unit should avoid entry of out of range values for all parameters, in case a safety relevant parameter value is being modified then before storing of the value in the second memory the second task, again executed by unit 34, provides for a range checking to verify if the newly entered value is within a predetermined range of acceptable values. In other words the same control unit executes a first range check before entering the value (first task) and a second range check after entry and storage of the new value in the first memory 35, but before storing the same in the second memory 36.

Another interesting feature of a possible embodiment provides that the main control unit 34 when executing the second task disables the possibility for modifying said region 44 (or regions (44, 46, 47)) until the capturing step is completed. It should be noted indeed that during data entry other tasks and activities are normally running in the unit 34; these activities could in principle cause a modification of said region(s) 44, 46, 47 before completion of the capture thereby compromising the reliability of the entire process and causing false alarms.

After having described the interaction between the main control unit 34 and the user interface, here below a detailed description of the control system architecture and of the type of interaction between said unit 34 and the various actuators and sensors of the medical apparatus is given.

As shown in FIG. 2, a first slave control unit 48 having a respective memory 49 is connected to the main control unit.

A second slave control unit 50 is also connected to the main control unit but not directly connected to the first slave control unit; also the second slave control unit has a respective memory 51.

A plurality of first actuators 53 are connected to and controlled by the slave control unit, but not directly controlled by the main control unit. In other words the main control unit can send control messages to said first actuators only through the first slave control unit 48. A plurality of first sensors 54 connected to the first slave control unit is present: these first sensors are not directly connected to the main control unit but exchange information with this latter only via the first slave control unit.

Finally a plurality of second sensors 55 is connected to the second slave control unit and not directly connected to the main control unit. These second sensors exchange information with the main unit 34 only via the second slave control unit.

As it is evident from FIG. 2, the first and second sensors are connected only to the first and second slave units respectively.

When entries are made via the user interface, the first task sends the values of any entered parameters to the first slave control unit, this latter being programmed for saving said values in its memory and for controlling said actuators so that the difference between the actual values sensed by the first sensors for said parameters and the set values of the corresponding parameters is within a range of acceptability. If the parameter under modification is safety relevant, then the second task sends the values of safety relevant parameters entered in the second memory to said second slave control unit, this latter being programmed for storing said values in its memory and for signalling if the difference between the actual values sensed by the second sensors for said parameters and the set values of the corresponding parameters in the memory of the second slave unit is outside a range of acceptability.

In other words the main unit 34, via the first control unit, controls the actuators and, using its first sensors for feedback, makes sure to really control the actuators so that the current values of the parameters tend to match the desired set values.

In parallel, for those parameters classified as safety relevant, the second slave control unit verifies if the values stored in its memory (which are coming from the second task) are really in line with those detected by the second sensors and actuated by the first actuators. This control made by the second slave unit is performed using information coming from the second sensors, which are separated and independent from the first sensors.

For sake of completeness and again referring to the embodiment of FIG. 1, the first and second sensors can comprise pressure sensors (as those indicate with 29), flow sensors (21,22 in FIG. 1), temperature sensors (not shown), conductivity sensors (16, 17 in FIG. 1), pH sensors (not shown), etcetera. Of course the nature and number of first and second sensors can vary depending upon the type of medical apparatus.

Finally, since the values of the parameters present in the second slave unit memory need to be correct, the second task comprises the step of periodically comparing the values of the parameters in the second memory to the values of the corresponding parameters in the memory of the second slave unit.

Notice that the apparatus 1 can include a plurality of first and second slave control units 48, 50 dedicated to corresponding subgroups of sensors and actuators. In any case all first slave units are connected to the main control unit and to the respective sensors and actuators but not directly connected to any of the second slave units. Analogously in case of more then one physical second slave unit, all second slave units are connected to their respective second sensors and to the main unit but not directly connected to any first slave unit.

Finally the second slave unit in the attached drawing is not controlling any actuators; however it is possible to have a number of second actuators (such as valve 27 and/or pumps 19, 20, 26) connected to the second slave unit so that in case of alarm conditions the second unit can put the machine in safety conditions for the patient. Notice that referring to the apparatus of FIG. 1, a bypass line directly connecting conduit 7 and 8 and bypassing the treatment unit 4 is present and can be opened by an actuator (valve or pump) controlled by the second slave unit upon occurrence or certain particularly critical alarms.

What has been just described in connection with data entry of a single parameter can be also applied in case of whole prescription entry.

When a prescription is loaded from an external database, it isn't immediately delivered: it is temporarily stored in a patient database.

According to a possible embodiment a user can see and modify the loaded set values in a prescription page; then he/she has to enter in a review page that summarizes all the prescription. When the user confirms the whole prescription, the main control unit saves all the set values in the first memory and then sends to a message to the second task that triggers the capture of the screen of the whole page. Then the second task sends a message indicating that a review process is starting.

The main control unit the continues executing the first task which shows a busy indicator on screen and sends as many messages to the second task as there are safety relevant set values in the prescription.

For each message, the second task performs the same check described in the previous part of this description: it compares the name, value and units of measure to reference bitmaps to detect any failures.

If the comparison gives a negative result, an alarm condition is generated which can even lead to the machine stop, otherwise the value is saved in the second memory and sent to the second slave unit. This review process is repeated for all safety relevant parameters. So, the actions after the user confirmation are:

| First task | Second task |
|---|---|
| save all the values in the first memory send the message to the second task | |
| | screen capture of the whole area send the review message to the GUI |
| show a busy indicator send the message for the first field to the second task | |
| | read the new value from the first memory check the value if ok, save it in the second memory otherwise generate alarm condition |
| send the message for the second field to the second task | |
| | read the new value from the first memory check the value if ok, save it in the second memory otherwise generate an alarm condition |
| . . . send the message review end to the second task | |
| | send the message review end to the main control unit once all messages have been processed |
| delete the busy indicator and the review page | |

The invention also concerns the method for setting up the above-described medical apparatuses, including a method for setting a blood treatment apparatus.

In particular the first steps of the method according to the invention are the setting of a new value for one or more parameters and the displaying of the new value of said parameter(s) in a region of the screen; the new value is stored in a normal memory, while the data representative of the region of the screen where at least the value of the entered parameter is being graphically displayed are stored in a video memory which can be part of the normal memory or not; the method then includes a step of capturing data representative of the region of the screen where at least the value of the entered parameter is being graphically displayed and a step of verifying if the value graphically displayed in the region (and represented by said representative data stored in the video memory) corresponds to the value stored in the normal memory. If said verification reveals identity between the value graphically represented in said region and the value entered in the memory, the method provides for storing said value in a further memory. In case of positive outcome of the verification the value is also displayed on the screen in an area distinct from the capture region.

The method also provides for verification of the unit of measure and of the parameter name as described above for the apparatus and therefore not further repeated. Also the details of the capture and verification steps are as above disclosed and not herein repeated.

The invention achieves important results.

Safety in data entry is further improved with no impact on usability. The fully automated procedures of the invention reduce at the minimum the possibility that wrong set values are really implemented by the machine: this is obtained without any substantial check by the operator thereby reducing possibility of human errors and enhancing ease in data entry.

The comparison of values actually displayed on screen with corresponding values actually entered in the machine memory insures a high degree of reliability and, at the same time, reduces the operator's activities.

Flexibility is also increased as the machine and method can be easily customized for different languages and numerical representations.

The invention claimed is:

1. Medical apparatus comprising:
    at least a user interface for enabling setting of a plurality of parameters pertinent to operation of said apparatus or pertinent to a treatment to be performed by said apparatus, the user interface including at least a screen for visualization of values of said parameters,
    a control system within said apparatus for controlling operation of said medical apparatus and responsive to actions by a user on said user interface,
    said control system including:
        a main control unit, connected to the user interface,
        a first memory connected to the main control unit,
        a video memory also connected to the main control unit for storing data corresponding to images visualized on said screen,
    said main control unit being programmed for executing the following steps:
        allowing setting of a new value for at least a parameter;
        displaying the new value on a region of the screen;
        storing the new value in the first memory;
        capturing from the video memory data representative of said region of the screen where at least the value of the entered parameter is being graphically displayed;
        verifying from said representative data if the value graphically displayed in said region corresponds to the value stored in said first memory;
        wherein said verification step includes the steps of converting the value entered in the first memory in data graphically representing said value; comparing the data graphically representing the value entered in the first memory to said data representative of the region of the screen where the value of the entered parameter is being displayed.

2. Medical apparatus according to claim 1, wherein the control system includes a second memory connected to the main control unit, and wherein after said verification step the main unit is programmed to execute a step of storing the value in the second memory if said verification reveals identity between the value graphically represented in said region and the value entered in the first memory.

3. Medical apparatus according to claim 2, wherein the main unit is programmed to execute a step of displaying the value stored in the second memory on a zone of the screen distinct from said region.

4. Medical apparatus according to claim 1, wherein the verification step includes the steps of: recognizing from said data the numeric value graphically represented in said region; and comparing said numeric value to the value of the same parameter stored in the first memory.

5. Medical apparatus according to claim 1, wherein the verification step comprises the following:
    referring to a plurality of sets of graphic data, each set being representative of a known pattern,
    comparing the captured data with the sets of graphic data for determining if the captured data contain an identifiable content;
    in case the captured data contain an identifiable content, comparing said identifiable content with value of the parameter stored in the first memory.

6. Medical apparatus according to claim 1, wherein, said recognition step comprising the following sub-steps:
    referring to a plurality of sets of graphic data, each set being representative of a known pattern;
    converting the value entered in the first memory in data graphically representing said value by using said sets of graphic data.

7. Medical apparatus according to claim 1, wherein:
    the main control unit is programmed to execute a first and a second task,
    the first task when executed by the control unit determining execution of said steps of allowing selection, modification and entry of the value in the first memory;
    the second task when executed by the control unit determining execution of said step of capturing data from the video memory and of said verification step,
    said second task being activated upon receipt from the first task of a new set message informing the second task that a new parameter value has been entered.

8. Medical apparatus according to claim 7, wherein the first task when executed by the main control unit determines a step of detecting if the value under modification refers to safety relevant parameters which are a subset of said plurality of parameters, said message is sent only in case of modification in the setting of safety relevant parameters.

9. Medical apparatus according to claim 8 comprising a dialysis liquid preparation module for preparing dialysis liquid to be sent into a blood treatment unit, and at least a waste line for receiving spent dialysate removed from the blood treatment unit.

10. Medical apparatus according to claim 9 comprising: a blood removal tubing, a blood return tubing, and a blood treatment unit having a first chamber connected to dialysis liquid preparation module and to the waste line, and a second chamber connected to the blood removal and to the blood return tubing, said first and second chamber being separated by a semipermeable membrane.

11. Medical apparatus according to claim 10, wherein the safety relevant parameters are one or more selected in the group comprising:
    Temperature of the dialysis liquid,
    Conductivity of the dialysis liquid,
    Flow rate of the dialysis liquid,
    Flow rate of the spent dialysate,
    Flow rate of the blood in the in one of said tubing,
    Ultrafiltration rate through the semipermeable membrane,
    Net weight loss rate,
    Treatment time,
    Weight loss.

12. Medical apparatus according to claim 1, wherein said capturing step comprises a step of capturing from video memory second data representative of a second region of the screen where the name of the entered parameter is being displayed, verifying if the name graphically displayed in said second region corresponds to a pre-stored name for the same parameter.

13. Medical apparatus according to claim 1, wherein said capturing step comprises a step of capturing from video memory third data representative of a third region of the screen where the unit of measure for the entered parameter is being displayed; verifying if said unit graphically displayed in said third region corresponds to a pre-stored unit of measure for the same parameter.

14. Medical apparatus according to claim 1, wherein said step of allowing setting of a new value comprises a step of range checking to verify if the value that is being set is within a predetermined range of acceptable values, and a subsequent step of activating the possibility to enter in the first memory said set value only if said range checking step is positively passed.

15. Medical apparatus according to claim 1, wherein said main control unit is programmed for executing the following steps before allowing setting of a new value for a parameter:
  displaying an indicium on said screen corresponding to a treatment parameter;
  allowing selection of the indicium for identifying the parameter a user intends to modify.

16. Medical apparatus according to claim 15, wherein:
the screen comprises a touch screen,
and wherein said step of allowing selection of the indicium comprises detecting a touching of said indicium,
said step of allowing setting of a parameter value comprises the following steps:
  in response to said touching, invoking a data-entry display on the touch screen said data entry display having at least two set buttons and an enter key;
  receiving a setting a parametric value corresponding to the treatment parameter by touching one or more buttons of the data-entry display;
  detecting the touching of said enter key for signifying setting has been completed and entering the set value.

17. Medical apparatus according to claim 15, wherein:
the screen comprises a touch screen,
the user interface comprises at least an enter hard key off of said touch screen and connected to the user interface,
and wherein:
said step of allowing selection of the indicium comprises detecting a touching of said indicium,
said step of allowing setting of a parameter value comprises the following steps:
  in response to said touching, invoking a data-entry display on a region of the touch screen said data entry display having at least two set buttons;
  receiving a setting a parametric value corresponding to the treatment parameter by touching one or more buttons of the data-entry display;
  detecting the touching of said enter key for signifying setting has been completed.

18. Medical apparatus according to claim 15, wherein:
the screen comprises a touch screen,
and wherein said step of allowing selection of the indicium comprises detecting a touching of said indicium,
said step of allowing setting of a parameter value comprises the following steps:
  in response to said touching, activating on the touch screen at least two set buttons and an enter key;
  receiving a setting a parametric value corresponding to the treatment parameter by touching one or more buttons;
  detecting the touching of said enter key for signifying setting has been completed.

19. Medical apparatus according to claim 1, wherein said main control unit is programmed for executing the step of allowing setting of a new value for a plurality of parameters; displaying the new values of the parameters on a region of the screen; storing the new values in the first memory; capturing from the video memory data representative of regions of the screen where the values of the entered parameters are graphically displayed; verifying from said representative data if the values graphically displayed in said regions correspond to the values stored in said first memory for the same respective parameters.

20. Medical apparatus according to claim 1, wherein if said verification reveals identity between the value graphically represented in said region and the value entered in the first memory, the main unit is programmed to execute a step of displaying the value stored in the first memory on a zone of the screen distinct from said region.

21. Medical apparatus comprising:
  at least a user interface for enabling setting of a plurality of parameters pertinent to operation of said apparatus or pertinent to a treatment to be performed by said apparatus, the user interface including at least a screen for visualization of values of said parameters,
  a control system within said apparatus for controlling operation of said medical apparatus and responsive to actions by a user on said user interface,
  said control system including:
    a main control unit, connected to the user interface,
    a first memory connected to the main control unit,
    a video memory also connected to the main control unit for storing data corresponding to images visualized on said screen,
  said main control unit being programmed for executing the following steps:
    allowing setting of a new value for at least a parameter;
    displaying the new value on a region of the screen;
    storing the new value in the first memory;
    capturing from the video memory data representative of said region of the screen where at least the value of the entered parameter is being graphically displayed;
    verifying from said representative data if the value graphically displayed in said region corresponds to the value stored in said first memory;
  wherein:
    the main control unit is programmed to execute a first and a second task,
    the first task when executed by the control unit determining execution of said steps of allowing selection, modification and entry of the value in the first memory;
    the second task when executed by the control unit determining execution of said step of capturing data from the video memory and of said verification step,
    said second task being activated upon receipt from the first task of a new set message informing the second task that a new parameter value has been entered.

22. Medical apparatus according to claim 21, wherein the verification step includes the steps of: recognizing from said data the numeric value graphically represented in said region; and comparing said numeric value to the value of the same parameter stored in the first memory.

23. Medical apparatus according to claim 21, wherein the verification step comprises the following:
  referring to a plurality of sets of graphic data, each set being representative of a known pattern,
  comparing the captured data with the sets of graphic data for determining if the captured data contain an identifiable content;

in case the captured data contain an identifiable content, comparing said identifiable content with value of the parameter stored in the first memory.

24. Medical apparatus according to claim 21, wherein said new message is sent by the control unit during execution of the first task only once the new value is stored in said first memory.

25. Medical apparatus according to claim 21, wherein said new set message contains the following information to allow the second task to perform the screen region capture:
information relating to the identity of message
information relating to coordinates of the screen region where the value is displayed.

26. Medical apparatus according to claim 21, wherein the second task when executed by the main control unit causes the step of periodically comparing the values of the parameters in the first memory to the values of the corresponding parameters in the second memory.

27. Medical apparatus according to claim 21, wherein the first task when executed by the main control unit determines a step of detecting if the value under modification refers to safety relevant parameters which are a subset of said plurality of parameters, said message is sent only in case of modification in the setting of safety relevant parameters.

28. Medical apparatus according to claim 21, wherein said second task when executed by the main control unit provides for the following consecutive steps to be executed after said verification step:
a range check step verifying if the value that is being set is within a predetermined range of acceptable values,
a step of storing the value in the second memory if at least the following conditions are both complied with: said verification reveals identity between the value graphically represented in said region and the value entered in the first memory, and the range checking step confirms the value is within said predetermined range.

29. Medical apparatus according to claim 21, wherein the second task when executed by the main control unit disables possibility for modifying said region until the capturing step is completed.

30. Medical apparatus according to claim 21 comprising:
a first slave main control unit connected to the main control unit, said first slave control unit having a respective memory,
a second slave main control unit connected to the main control unit but not directly connected to the first slave main control unit, said second slave control unit having a respective memory,
a plurality of first actuators connected to and controlled by the slave main control unit and not directly controlled by the main control unit,
a plurality of first sensors connected to the first slave control unit and not directly connected to the main control unit,
a plurality of second sensors connected to the second slave control unit and not directly connected to the main control unit
the first task sending the values of any entered parameters to the first slave control unit, this latter being programmed for saving said values in its memory and for controlling said actuators so that the difference between the actual values sensed by the first sensors for said parameters and the set values of the corresponding parameters is within a range of acceptability,
the second task sending the values of safety relevant parameters entered in the second memory to said second slave control unit, this latter being programmed for storing said values in its memory and for signalling if the difference between the actual values sensed, by the second sensors for said parameters and the set values of the corresponding parameters in the memory of the second slave unit is outside a range of acceptability.

31. Medical apparatus according to claim 30, wherein the second task comprises the step of periodically comparing the values of the parameters in the second memory to the values of the corresponding parameters in the memory of the second slave unit.

32. Medical apparatus comprising:
at least a user interface for enabling setting of a plurality of parameters pertinent to operation of said apparatus or pertinent to a treatment to be performed by said apparatus, the user interface including at least a screen for visualization of values of said parameters,
a control system within said apparatus for controlling operation of said medical apparatus and responsive to actions by a user on said user interface,
said control system including:
a main control unit, connected to the user interface,
a first memory connected to the main control unit,
a video memory also connected to the main control unit for storing data corresponding to images visualized on said screen,
said main control unit being programmed for executing the following steps:
allowing setting of a new value for at least a parameter;
displaying the new value on a region of the screen;
storing the new value in the first memory;
capturing from the video memory data representative of said region of the screen where at least the value of the entered parameter is being graphically displayed;
verifying from said representative data if the value graphically displayed in said region corresponds to the value stored in said first memory;
wherein said main control unit is programmed for executing the step of allowing setting of a new value for a plurality of parameters; displaying the new values of the parameters on a region of the screen; storing the new values in the first memory; capturing from the video memory data representative of regions of the screen where the values of the entered parameters are graphically displayed; verifying from said representative data if the values graphically displayed in said regions correspond to the values stored in said first memory for the same respective parameters.

33. Medical apparatus according to claim 32, wherein the verification step includes the steps of: recognizing from said data the numeric value graphically represented in said region; and comparing said numeric value to the value of the same parameter stored in the first memory.

34. Medical apparatus according to claim 32, wherein the verification step comprises the following:
referring to a plurality of sets of graphic data, each set being representative of a known pattern,
comparing the captured data with the sets of graphic data for determining if the captured data contain an identifiable content;
in case the captured data contain an identifiable content, comparing said identifiable content with value of the parameter stored in the first memory.

35. Medical apparatus according to claim 32, wherein:
the main control unit is programmed to execute a first and a second task, the first task when executed by the control unit determining execution of said steps of allowing selection, modification and entry of the value in the first memory;

the second task when executed by the control unit determining execution of said step of capturing data from the video memory and of said verification step, said second task being activated upon receipt from the first task of a new set message informing the second task that a new parameter value has been entered.

36. Medical apparatus comprising:

at least a user interface for enabling setting of a plurality of parameters pertinent to operation of said apparatus or pertinent to a treatment to be performed by said apparatus, the user interface including at least a screen for visualization of values of said parameters, a control system within said apparatus for controlling operation of said medical apparatus and responsive to actions by a user on said user interface, said control system including:
    a main control unit, connected to the user interface,
    a first memory connected to the main control unit,
    a video memory also connected to the main control unit for storing data corresponding to images visualized on said screen, said main control unit being programmed for executing the following steps:
    allowing setting of a new value for at least a parameter;
    displaying the new value on a region of the screen;
    storing the new value in the first memory;
    capturing from the video memory data representative of said region of the screen where at least the value of the entered parameter is being graphically displayed;
    verifying from said representative data if the value graphically displayed in said region corresponds to the value stored in said first memory;
    wherein if said verification reveals identity between the value graphically represented in said region and the value entered in the first memory, the main unit is programmed to execute a step of displaying the value stored in the first memory on a zone of the screen distinct from said region.

37. Medical apparatus according to claim 36, wherein the verification step includes the steps of: recognizing from said data the numeric value graphically represented in said region; and comparing said numeric value to the value of the same parameter stored in the first memory.

38. Medical apparatus according to claim 36, wherein the verification step comprises the following:
    referring to a plurality of sets of graphic data, each set being representative of a known pattern,
    comparing the captured data with the sets of graphic data for determining if the captured data contain an identifiable content;
    in case the captured data contain an identifiable content, comparing said identifiable content with value of the parameter stored in the first memory.

39. Medical apparatus according to claim 36, wherein:
    the main control unit is programmed to execute a first and a second task,
    the first task when executed by the control unit determining execution of said steps of allowing selection, modification and entry of the value in the first memory;
    the second task when executed by the control unit determining execution of said step of capturing data from the video memory and of said verification step,
    said second task being activated upon receipt from the first task of a new set message informing the second task that a new parameter value has been entered.

40. Medical apparatus comprising:

at least a user interface for enabling setting of a plurality of parameters pertinent to operation of said apparatus or pertinent to a treatment to be performed by said apparatus, the user interface including at least a screen for visualization of values of said parameters, a control system within said apparatus for controlling operation of said medical apparatus and responsive to actions by a user on said user interface, said control system including:
    a main control unit, connected to the user interface,
    a first memory connected to the main control unit,
    a video memory also connected to the main control unit for storing data corresponding to images visualized on said screen, said main control unit being programmed for executing the following steps:
    allowing setting of a new value for at least a parameter;
    displaying the new value on a region of the screen;
    storing the new value in the first memory;
    capturing from the video memory data representative of said region of the screen where at least the value of the entered parameter is being graphically displayed;
    verifying from said representative data if the value graphically displayed in said region corresponds to the value stored in said first memory;
    wherein the verification step includes the steps of: recognizing from said data the numeric value graphically represented in said region; and comparing said numeric value to the value of the same parameter stored in the first memory.

41. Medical apparatus according to claim 40, wherein the control system includes a second memory connected to the main control unit, and wherein after said verification step the main unit is programmed to execute a step of storing the value in the second memory if said verification reveals identity between the value graphically represented in said region and the value entered in the first memory.

42. Medical apparatus according to claim 40, wherein said capturing step comprises a step of capturing from video memory second data representative of a second region of the screen where the name of the entered parameter is being displayed, verifying if the name graphically displayed in said second region corresponds to a pre-stored name for the same parameter.

43. Medical apparatus according to claim 40, wherein said capturing step comprises a step of capturing from video memory third data representative of a third region of the screen where the unit of measure for the entered parameter is being displayed; verifying if said unit graphically displayed in said third region corresponds to a pre-stored unit of measure for the same parameter.

44. Medical apparatus according to claim 40, wherein said step of allowing setting of a new value comprises a step of range checking to verify if the value that is being set is within a predetermined range of acceptable values, and a subsequent step of activating the possibility to enter in the first memory said set value only if said range checking step is positively passed.

45. Medical apparatus according to claim 40, wherein said main control unit is programmed for executing the following steps before allowing setting of a new value for a parameter:
    displaying an indicium on said screen corresponding to a treatment parameter;

allowing selection of the indicium for identifying the parameter a user intends to modify.

46. Medical apparatus according to claim 45, wherein:
the screen comprises a touch screen,
and wherein said step of allowing selection of the indicium comprises detecting a touching of said indicium,
said step of allowing setting of a parameter value comprises the following steps:
   in response to said touching, invoking a data-entry display on the touch screen said data entry display having at least two set buttons and an enter key;
   receiving a setting a parametric value corresponding to the treatment parameter by touching one or more buttons of the data-entry display;
   detecting the touching of said enter key for signifying setting has been completed and entering the set value.

47. Medical apparatus according to claim 45, wherein:
the screen comprises a touch screen,
the user interface comprises at least an enter hard key off of said touch screen and connected to the user interface,
and wherein:
said step of allowing selection of the indicium comprises detecting a touching of said indicium,
said step of allowing setting of a parameter value comprises the following steps:
   in response to said touching, invoking a data-entry display on a region of the touch screen said data entry display having at least two set buttons;
   receiving a setting a parametric value corresponding to the treatment parameter by touching one or more buttons of the data-entry display;
   detecting the touching of said enter key for signifying setting has been completed.

48. Medical apparatus according to claim 45, wherein:
the screen comprises a touch screen,
and wherein said step of allowing selection of the indicium comprises detecting a touching of said indicium,
said step of allowing setting of a parameter value comprises the following steps:
   in response to said touching, activating on the touch screen at least two set buttons and an enter key;
   receiving a setting a parametric value corresponding to the treatment parameter by touching one or more buttons;
   detecting the touching of said enter key for signifying setting has been completed.

49. Medical apparatus according to claim 40, wherein:
the main control unit is programmed to execute a first and a second task,
the first task when executed by the control unit determining execution of said steps of allowing selection, modification and entry of the value in the first memory;
the second task when executed by the control unit determining execution of said step of capturing data from the video memory and of said verification step,
said second task being activated upon receipt from the first task of a new set message informing the second task that a new parameter value has been entered, and wherein
the first task when executed by the main control unit determines a step of detecting if the value under modification refers to safety relevant parameters which are a subset of said plurality of parameters, said message is sent only in case of modification in the setting of safety relevant parameters, the medical apparatus further comprising a dialysis liquid preparation module for preparing dialysis liquid to be sent into a blood treatment unit, and at least a waste line for receiving spent dialysate removed from the blood treatment unit.

50. Medical apparatus according to claim 49, comprising:
a blood removal tubing, a blood return tubing, and a blood treatment unit having a first chamber connected to dialysis liquid preparation module and to the waste line, and a second chamber connected to the blood removal and to the blood return tubing, said first and second chamber being separated by a semipermeable membrane.

51. Medical apparatus according to claim 50, wherein the safety relevant parameters are one or more selected in the group comprising:
Temperature of the dialysis liquid,
Conductivity of the dialysis liquid,
Flow rate of the dialysis liquid,
Flow rate of the spent dialysate,
Flow rate of the blood in the in one of said tubing,
Ultrafiltration rate through the semipermeable membrane,
Net weight loss rate,
Treatment time
Weight loss.

52. Medical apparatus according to claim 40, wherein the verification step comprises the following:
   referring to a plurality of sets of graphic data, each set being representative of a known pattern,
   comparing the captured data with the sets of graphic data for determining if the captured data contain an identifiable content;
   in case the captured data contain an identifiable content, comparing said identifiable content with value of the parameter stored in the first memory.

53. Medical apparatus comprising:
at least a user interface for enabling setting of a plurality of parameters pertinent to operation of said apparatus or pertinent to a treatment to be performed by said apparatus, the user interface including at least a screen for visualization of values of said parameters,
a control system within said apparatus for controlling operation of said medical apparatus and responsive to actions by a user on said user interface,
said control system including:
   a main control unit, connected to the user interface,
   a first memory connected to the main control unit,
   a video memory also connected to the main control unit for storing data corresponding to images visualized on said screen,
said main control unit being programmed for executing the following steps:
   allowing setting of a new value for at least a parameter;
   displaying the new value on a region of the screen;
   storing the new value in the first memory;
   capturing from the video memory data representative of said region of the screen where at least the value of the entered parameter is being graphically displayed;
   verifying from said representative data if the value graphically displayed in said region corresponds to the value stored in said first memory;
wherein the control system includes a second memory connected to the main control unit, and wherein after said verification step the main unit is programmed to execute a step of storing the value in the second memory if said verification reveals identity between the value graphically represented in said region and the value entered in the first memory; and further wherein the main unit is programmed to execute a step of displaying the value stored in the second memory on a zone of the screen distinct from said region.

54. Medical apparatus according to claim 53, wherein the verification step includes the steps of: recognizing from said data the numeric value graphically represented in said region; and comparing said numeric value to the value of the same parameter stored in the first memory.

55. Medical apparatus according to claim 53, wherein the verification step comprises the following:

referring to a plurality of sets of graphic data, each set being representative of a known pattern, comparing the captured data with the sets of graphic data for determining if the captured data contain an identifiable content;

in case the captured data contain an identifiable content, comparing said identifiable content with value of the parameter stored in the first memory.

56. Medical apparatus according to claim 53, wherein:

the main control unit is programmed to execute a first and a second task, the first task when executed by the control unit determining execution of said steps of allowing selection, modification and entry of the value in the first memory;

the second task when executed by the control unit determining execution of said step of capturing data from the video memory and of said verification step, said second task being activated upon receipt from the first task of a new set message informing the second task that a new parameter value has been entered.

* * * * *

UNITED STATES PATENT AND TRADEMARK OFFICE
CERTIFICATE OF CORRECTION

PATENT NO. : 7,922,899 B2
APPLICATION NO. : 11/916655
DATED : April 12, 2011
INVENTOR(S) : Vasta et al.

It is certified that error appears in the above-identified patent and that said Letters Patent is hereby corrected as shown below:

At column 18, line 2, please delete the "," after "sensed" and before "by".

Signed and Sealed this
Twenty-eighth Day of June, 2011

David J. Kappos
*Director of the United States Patent and Trademark Office*